(12) United States Patent
Stoschek

(10) Patent No.: US 6,797,236 B2
(45) Date of Patent: Sep. 28, 2004

(54) DESIGN AND SIGNAL RECOVERY OF BIOMOLECULAR SENSOR ARRAYS

(75) Inventor: Arne Stoschek, Palo Alto, CA (US)

(73) Assignee: Infineon Technologies AG, Munich (DE)

( * ) Notice: Subject to any disclaimer, the term of this patent is extended or adjusted under 35 U.S.C. 154(b) by 476 days.

(21) Appl. No.: 10/051,803

(22) Filed: Jan. 14, 2002

(65) Prior Publication Data

US 2003/0134429 A1 Jul. 17, 2003

(51) Int. Cl.$^7$ .................. G01N 21/01; G01N 27/00; G01N 27/27; G01N 33/48
(52) U.S. Cl. .............. 422/55; 204/403.01; 204/403.03; 422/56; 422/57; 422/58; 422/81; 422/82.01; 422/82.02; 422/82.03; 422/82.04; 422/82.05; 422/82.06; 422/82.07; 422/82.08; 422/82.09; 422/86; 422/98; 436/149; 436/150; 436/151; 436/164; 436/169; 436/171; 436/172; 436/183
(58) Field of Search .............................. 422/52, 55–58, 422/81, 82.01–82.09, 83, 86, 90–91, 98; 204/403.01, 403.03; 436/149–151, 164, 169, 171–172, 183

(56) References Cited

U.S. PATENT DOCUMENTS

| | | | | |
|---|---|---|---|---|
| 4,627,893 A | * | 12/1986 | Cormier et al. ............. | 205/779 |
| 4,640,821 A | * | 2/1987 | Mody et al. .................. | 422/81 |
| 5,194,133 A | * | 3/1993 | Clark et al. ................. | 204/608 |
| 5,262,305 A | * | 11/1993 | Heller et al. ............. | 205/780.5 |
| 5,416,026 A | * | 5/1995 | Davis .......................... | 436/66 |
| 5,730,938 A | * | 3/1998 | Carbonari et al. ............ | 422/64 |
| 5,886,348 A | * | 3/1999 | Lessure et al. ......... | 250/339.13 |
| 6,359,283 B1 | * | 3/2002 | Gordon et al. ......... | 250/370.13 |

FOREIGN PATENT DOCUMENTS

JP          58-171359        * 10/1983

OTHER PUBLICATIONS

Albert, K. J. et al, Analytical Chemistry 2000, 72, 1947–1955.*
Klett, O. et al, Analytical Chemistry 2001, 73, 1909–1915.*
Lu, H. B. et al, Chemical Abstracts 2001, 134, abstract 350108.*

* cited by examiner

Primary Examiner—Arlen Soderquist

(57) ABSTRACT

The present invention provides an apparatus and method of reducing noise associated with biomolecular measurement systems. Sensor detection system noise characteristics in the presence of other sensor detection systems are determined and advantageously used to determine an arrangement of the individual sensor cells. The sensor cells are arranged on a substrate such that the system noise is determinable and can thus be filtered from the measurement signal.

23 Claims, 2 Drawing Sheets

DESIGN AND SIGNAL RECOVERY OF BIOMOLECULAR SENSOR ARRAYS

FIELD OF THE INVENTION

The present invention relates to micro sensors and, more particularly, to biomolecular sensor array design.

BACKGROUND OF THE INVENTION

Micro sensors and, more particularly, biosensors have attracted much attention lately due to their increasing utility in the pharmaceutical, chemical and biological arenas. Biosensors have been developed to detect a variety of biomolecular complexes including oligonucleotide pairs, antibody-antigen, hormone-receptor, enzyme-substrate and lectin-glycoprotein interactions, for example. In general, biosensors are comprised of two components: a molecular recognition element and a transducing structure that converts the molecular recognition event into a quantifiable signal. Signal transductions are generally accomplished with electrochemical, field-effect transistor, optical absorption, fluorescence or interferometric devices.

Generally, an array of biosensors are used for the execution of biomedical and biomolecular measurements in which the state of the biological system is translated into a response at a specific sensor location. Protein-microarrays or DNA-microarrays are examples of biomolecular sensor arrays. Biomolecular sensor arrays are comprised of individual sensors cells organized in some fashion, such as on a rectangular grid.

The output of the biomolecular sensor array is multidimensional data in which each sensor cell (i.e. each data point in the array) codes the response of a specific experiment. The number of sensor cells, i.e. of events to be measured, can be large, e.g. 10,000. Though there have been many advancements in the area of biosensors, in practice, biomolecular sensor arrays tend to provide noisy data. The noise in the data limits the reliability of conclusions that can be drawn from the measurements. Widespread application of current biomolecular sensor arrays is hampered by the unreliability of the obtained data and the poor reproducibility of results.

Two techniques commonly used to improve on the reliability of the obtained data of the biomolecular sensor arrays include signal processing methods and data averaging methods. Statistical signal processing methods, such as principal component analysis, are applied after recording of the noisy measurements. These methods are intended to detect improbable values at individual sensor cells, such as outliers. Although theses methods may be able to detect if a value at an individual sensor cell is unreliable, they cannot recover the value itself.

Data averaging methods average data over repeated instances of the same measurement at several sensor cells and applies the average to reduce noise in the individual measurements. Averaging over a number of repeated instances of the same measurement at a number of sensor cells can reduce certain types of noise in the individual measurements. For example, random additive Gaussian noise can be reduced by a factor of approximately $1/\sqrt{n}$. However, a substantial noise reduction would require a high redundancy in the measurements which would be prohibitively expensive. Furthermore, averaging does not improve on certain types of noise, such as multiplicative noise or systematic errors.

SUMMARY OF THE INVENTION

The present invention achieves technical advantages as an apparatus and method of reducing noise associated with biomolecular measurement systems. Sensor detection system noise characteristics in the presence of other sensor detection systems are determined and advantageously used to determine an arrangement of the individual sensor cells. The sensor cells are arranged on a substrate such that the system noise is determinable and can thus be filtered from the measurement signal.

DETAILED DESCRIPTION

Figure 1:
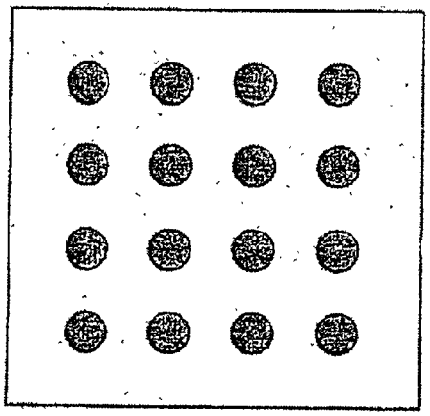
FIG. 1 illustrates a simplified diagram of an exemplary biomolecular sensor array with 4-by-4 sensor cell arrangement.

The numerous innovative teachings of the present application will be described with particular reference to the presently preferred exemplary embodiments. However, it should be understood that this class of embodiments provides only a few examples of the many advantageous uses and innovative teachings herein. In general, statements made in the specification of the present application do not necessarily delimit any of the various claimed inventions. Moreover, some statements may apply to some inventive features, but not to others.

Throughout the drawings, it is noted that the same reference numerals or letters will be used to designate like or equivalent elements having the same function. Detailed descriptions of known functions and constructions unnecessarily obscuring the subject matter of the present invention have been omitted for clarity.

Referring now to FIG. 1 there is illustrated a simplified diagram of an exemplary biomolecular sensor array with a 4-by-4 sensor cell arrangement. Biomolecular sensor arrays can comprise of up to several thousand individual sensors cells that are generally organized on a support grid in some non-random and defined fashion, such as the rectangular grid arrangement shown in FIG. 1 (only 16 sensor cells are shown for simplicity), in which each individual sensor cell performs a measurement.

Patterning of a support grid may be done in a number of different ways appreciated by those knowledgeable in the microfabrication arts. A device is typically produced by first selecting a substrate material and producing a patterned support grid for the sensor cells.

Commonly, sensor cells of a sensor array are designed to detect the same or similar types of biomolecular complexes (such as oligonucleotide pairs), and are based on the same sensor principle. Most widely used sensor principles are based on electrochemical, field-effect transistor, optical absorption, fluorescence or interferometric devices. Differently adapted sensor cells are combined on one array in order to effectively carry out a large number of individual measurements or experiments. Currently, organization of the sensor cells in this combination arrangement is not taken into consideration with respect to data processing issues.

The measured value at each sensor cell is intended to be representative of a certain state of a biological system under scrutiny, such as DNA in relation to a certain disease. These sensor principles have the common problem of producing a noisy signal which contains the true data corrupted by noise. The sources of noise are generally associated with: 1) biomolecular sample preparation and (2) sensor deficiencies. The noise level for different sensor principles can vary. The noise can be a mix of different types, such as additive, multiplicative and systematic noise. The reproducibility of a measured value (given a certain expected accuracy) can be as low as 30% in which systematic errors contribute a substantial part to the overall measurement error.

In accordance with an embodiment of the present invention, sensor cells are arranged in an array such that individual measurements from a plurality of sensor cells are cooperative to either diminish or cancel out respective systematic noise using combinatorial methods or reduce noise by applying error correction or signal recovery methods.

An aspect of the present invention is to arrange the sensor cells on the sensor array such that predetermined statistical dependencies between sensor cells can be utilized to reduce the systematic noise when performing measurements with a combinational sensor array. The rationale behind this approach is the interdependence between the noise of a sensor array and the statistical dependencies between sensor cells on the array. It is assumed that these statistical dependencies can be determined for a given type of sensor array, sensor type, and specific measurement to be carried out.

Specifically, the statistical dependencies can be determined by comparing (i) redundant measurements of the same biological instance using the same type of sensor cell on a sensor array, and/or (ii) different measurements using different types of sensor cells on a sensor array where the location of the sensor cells on the array is varied. The statistical dependencies are characterized by spatial extend or orientation on the sensor array, given a sensor principle, sensor type, and/or biomolecular complexes to be detected.

Figure 2:
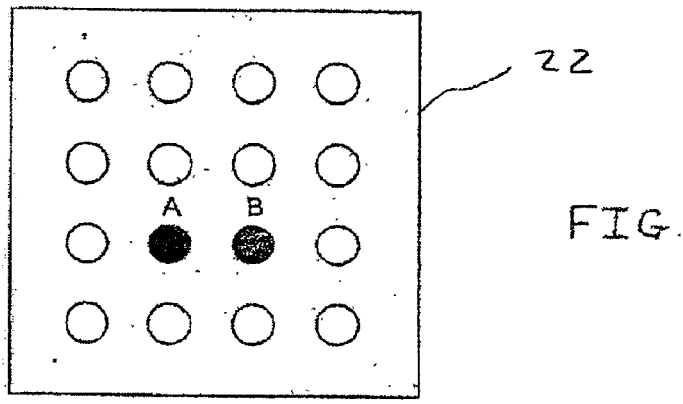
FIG. 2 shows a simplified diagram of a biomolecular sensor array illustrating a spatial arrangement of sensor cells in accordance with an exemplary embodiment of the present invention.

Referring now to FIG. 2 there is illustrated a biomolecular sensor array 22 in accordance with an exemplary embodiment of the present invention. In this simple example, a sensor cell of a first type (A) is determined to exhibit a reproducible systematic error or noise of amount approximately "x" whenever placed adjacent to (at a predetermined distance from) a sensor cell of a second type (B) on the surface of the sensor array 22. In accordance with the present invention, an improved sensor array 22 is arranged such that the A type sensor cell is positioned the predetermined distance from a B type sensor cell. Since the error in the A type sensor cell is known for this spatial arrangement, the measured value of the A type sensor cell is directly recoverable by simply subtracting or otherwise filtering the known systematic error "x". For an arrangement which includes many other A type sensor cells, a B type sensor cell is positioned at the predetermined distance from each A type sensor cell. This simple example assumes that the A and B type sensors are not substantially influenced by other sensor cells on the sensor array 22, such as by a third type (C).

Figure 3:
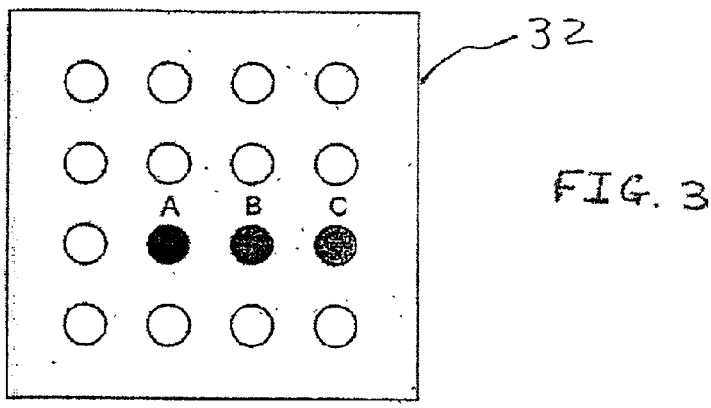
FIG. 3 shows another simplified diagram of a biomolecular sensor array illustrating a spatial arrangement of sensor cells in accordance with an exemplary embodiment of the present invention.

Referring now to FIG. 3 there is illustrated another biomolecular sensor array 32 in accordance with an exemplary embodiment of the present invention. In this example, the A type sensor cell is determined to exhibit, in addition to the condition described in the previous example with regard to B type sensor cells, a reproducible systematic error or noise amount of approximately "−x" whenever placed at a distance of two sensor cell positions (twice the predetermined distance) from a C type sensor cell. In accordance with the present invention, the improved sensor array 32 is arranged such that the A type sensor cell is positioned next to a B type sensor cell and two sensor cell positions away from a C type sensor cell. Since the error in the A type sensor cell is known, the measured value of the A type sensor cell is directly recoverable by simply applying the known systematic errors and in this case the known systematic errors of the A type sensor cell cancel-out (where "x"+"−x"=0).

In both of the above-mentioned exemplary embodiments, B type sensor cells and C type sensor cells can be redundantly placed on the sensor array 32 for the reason to enable the signal recovery on the A type sensor cell. For simplicity, A, B, and C type sensor cells are assumed not to be influenced by other types of sensor cells on the sensor array 32. In one embodiment, the strategy for the spatial organization of sensor cells on the sensor array 32 is to spatially separate types of sensor cells with strong and weak statistical dependency which reduces complexity in the signal recovery algorithms. For example, neighboring sensor cells can exhibit either strong statistical dependencies (i.e. they influence each other significantly) or weak statistical dependencies (i.e. they do not significantly influence each other). A method for arranging the sensor cells on a sensor array is to group the sensor cells such that strong statistical dependencies can be used for signal recovery and other (unwanted) statistical dependencies do not interfere the signal recovery. Say, on one sensor array, sensor cells A and B exhibit a usable strong statistical dependency between them. Further, sensor cells C and D exhibit a usable strong statistical dependency between them but not towards A and B. Furthermore, E and F exhibit a usable strong statistical dependency between them as well as exhibiting some other type of strong statistical dependency towards A, B, C, and D. In this case, (A, B) can be placed next to (C, D), however, (E, F) should be separate from the latter pairs. Thus, the spatial organization becomes an optimization problem with respect to the overall recoverability for sensor cells on the sensor array 32.

Figure 4:
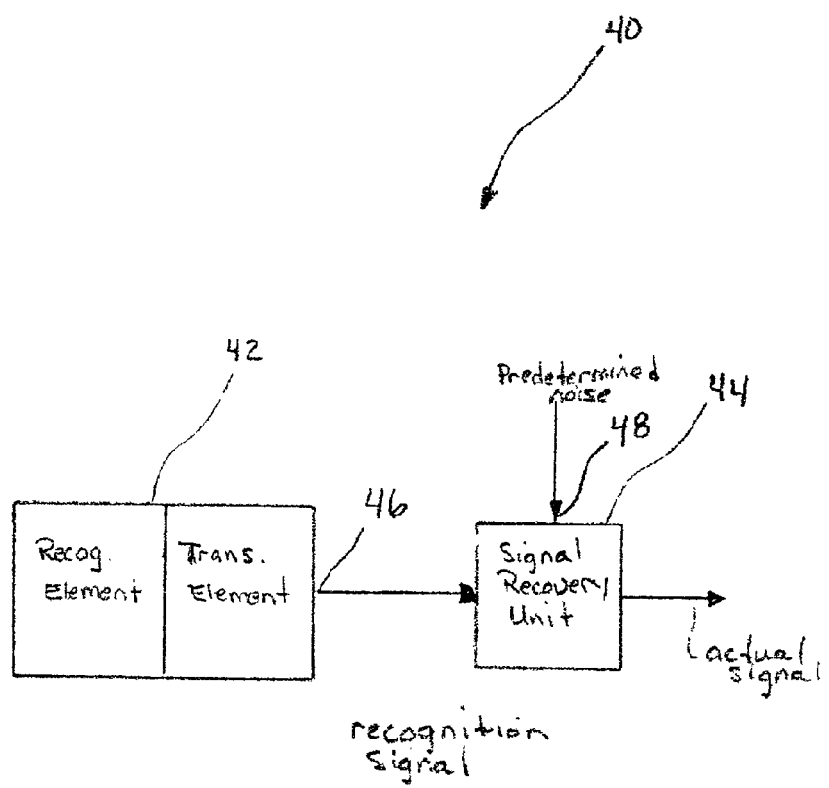
FIG. 4 illustrates a simplified diagram of a sensor cell detection system in accordance with an exemplary embodiment of the present invention.

Referring now to FIG. 4 there is illustrated a simplified diagram of a sensor cell detection system 40 in accordance with an exemplary embodiment of the present invention. The sensor cell detection system 40 comprises a sensor cell 42 and a signal recovery unit 44. The sensor cell 42 includes a molecular recognition element adapted to detect a molecular event and a transducing element adapted to convert molecular recognition into a signal. The recognition signal is output at 46 to the signal recovery unit 44.

The signal recovery unit 44 also receives at input 48 an indication of the system noise of the sensor cell 42 determined from the spatial dependencies as above-described. Responsive to this indication of the system noise at 48, the signal recovery unit 44 filters (e.g. subtracts) the system noise from the received recognition signal and outputs a corresponding noise-filtered measurement signal of the sensor cell 42. The signal recovery unit 44 can also be adapted to support a plurality of sensor cells. It should be noted that alternative methods such as simple averaging of redundant measurements do not make use of prior knowledge about the type of error and the error statistics in the sensor array in order to recover a measurement signal out of noisy data.

Although a preferred embodiment of the method and system of the present invention has been illustrated in the accompanied drawings and described in the foregoing Detailed Description, it is understood that the invention is not limited to the embodiments disclosed, but is capable of numerous rearrangements, modifications, and substitutions without departing from the spirit of the invention as set forth and defined by the following claims.

What is claimed is:

1. An apparatus for detecting molecular presence, comprising:

a substrate adapted to support an arrangement of sensor cells for detecting molecular presence;

a plurality of first sensor cells supported on said substrate;

each of said first sensor cells having an output adapted to output a recognition signal responsive to detection of molecular presence by the associated first sensor cell; and a plurality of second sensor cells supported on said substrate, each said recognition signal including noise which can be approximated based on a position of one of said second sensor cells relative to the associated first sensor cell on said substrate, said first sensor cells and said second sensor cells arranged on said substrate such that at least one of said second sensor cells occupies said position relative to each of said first sensor cells.

2. The apparatus of claim 1 further comprising a signal recovery unit having a first input coupled to one of said first sensor cells for receiving the associated recognition signal and a second input for receiving an indication of the associated noise, said signal recovery unit responsive to said noise indication for filtering the associated noise from said recognition signal.

3. The apparatus of claim 2, wherein said signal recovery unit is for subtracting said noise from said recognition signal.

4. The apparatus of claim 1, wherein said position is defined by a first distance between the associated first and second sensor cells.

5. The apparatus of claim 4, wherein said first sensor cells and said second sensor cells are arranged in an ordered fashion on said substrate such that adjacent sensor cells are separated by said first distance.

6. The apparatus of claim 1, wherein said first sensor cells comprise a molecular recognition element and a transducing element coupled to said molecular recognition element for converting a molecular recognition event into said recognition signal.

7. The apparatus of claim 1, wherein said second sensor cells adapted for detection of a further molecular presence.

8. The apparatus of claim 1 further comprising a plurality of third sensor cells supported on said substrate, each said recognition signal including further noise which can be approximated based on a further position of one of said third sensor cells relative to the associated first sensor cell on said substrate, said third sensor cells arranged on said substrate such that at least one of said third sensor cells occupies said further position relative to each of said first sensor cells.

9. The apparatus of claim 8 further comprising a signal recovery unit having a first input coupled to one of said first sensor cells for receiving the associated recognition signal and a second input for receiving an indication of the associated noise, said signal recovery unit responsive to said noise indication for filtering the associated noise from said recognition signal.

10. The apparatus of claim 9, wherein said signal recovery unit is for subtracting said noise from said recognition signal.

11. The apparatus of claim 8, wherein said position is defined by a first distance between the associated first and second sensor cells and said further position is defined by a second distance between the associated first and third sensor cells, said first sensor cells and said second sensor cells and said third sensor cells further arranged in an ordered fashion on said substrate such that adjacent sensor cells are separated by said first distance.

12. The apparatus of claim 11, wherein said second distance is greater than said first distance.

13. The apparatus of claim 8, wherein said second and third sensor cells are adapted for detection of further respective molecular presences.

14. A method of arranging on a substrate a plurality of first sensor cells and a plurality of second sensor cells for detection of molecular presence, comprising:

determining that noise associated with an indication of molecular presence by any of said first sensor cells can be approximated based on a position of one of said second sensor cells relative to the first sensor cell on said substrate; and arranging said first sensor cells and said second sensor cells on said substrate such that at least one of said second sensor cells occupies said position relative to each of said first sensor cells.

15. The method of claim 14 further comprising filtering said noise from a molecular presence indication by one of the first sensor cells responsive to an associated noise indication.

16. The method of claim 15, wherein said filtering step includes subtracting said noise from said molecular presence indication.

17. The method of claim 14, wherein said position is defined by a first distance between the associated first and second sensor cells.

18. The method of claim 17 further comprising arranging said first sensor cells and said second sensor cells in an ordered fashion on said substrate such that adjacent sensor cells are separated by said first distance.

19. A method of arranging on a substrate a plurality of first sensor cells, a plurality of second sensor cells and a plurality of third sensor cells for detection of molecular presence, comprising:

determining that noise associated with an indication of molecular presence by any of said first sensor cells can be approximated based on a position of one of said second sensor cells relative to the first sensor cell on said substrate;

determining that further noise associated with an indication of molecular presence by any of said first sensor cells can be approximated based on a further position of one of said third sensor cells relative to the first sensor cell on said substrate; and arranging said first sensor cells and said second sensor cells and said third sensor cells on said substrate such that at least one of said second sensor cells occupies said position relative to each of said first sensor cells and at least one of said third sensor cells occupies said further position relative to each of said first sensor cells.

20. The method of claim 19 further comprising filtering said noise and said further noise from said molecular presence indication responsive to an associated noise indication.

21. The method of claim 19, wherein said position is defined by a first distance between the associated first and second sensor cells and said further position is defined by a second distance between the associated first and third sensor cells.

22. The method of claim 21 further comprising arranging said first sensor cells and said second sensor cells and said third sensor cells in an ordered fashion on said substrate such that adjacent sensor cells are separated by said first distance.

23. The method of claim 22, wherein said second distance is greater than said first distance.

* * * * *